United States Patent [19]

Leslie et al.

[11] Patent Number: 4,896,303

[45] Date of Patent: Jan. 23, 1990

[54] METHOD FOR CEMENTATION EVALUATION USING ACOUSTICAL COUPLING AND ATTENUATION

[75] Inventors: David Leslie; Jacques A. E. de Selliers de Moranville; Dennis J. Pittman, all of Houston, Tex.

[73] Assignee: Schlumberger Technology Corporation, Houston, Tex.

[21] Appl. No.: 273,120

[22] Filed: Nov. 17, 1988

Related U.S. Application Data

[63] Continuation of Ser. No. 913,820, Sep. 30, 1986, abandoned.

[51] Int. Cl.[4] .............................................. G01V 1/40
[52] U.S. Cl. ...................................... 367/35; 364/422; 367/30; 367/31
[58] Field of Search ...................... 367/30, 31, 32, 35; 181/105; 364/422

[56] References Cited

U.S. PATENT DOCUMENTS

| | | | |
|---|---|---|---|
| 3,909,775 | 9/1975 | Lavigne | 181/105 |
| 4,203,324 | 5/1980 | Baumael | 367/908 |
| 4,255,798 | 3/1981 | Havira | 367/35 |
| 4,551,823 | 11/1985 | Carmichael et al. | 367/35 |
| 4,703,427 | 10/1987 | Atala et al. | 367/31 |
| 4,709,357 | 11/1987 | Maki | 367/35 |
| 4,805,156 | 2/1989 | Attali et al. | 367/35 |

OTHER PUBLICATIONS

Communication no 42, "Fracture Detection Using the Sonic Tool", by; Philippe S. Y. Cheung.
SPE 13044 "The Fluid-Compensated Cement Bond Log", by: T. H. Nayfeh, W. B. Wheelis, Jr., and H. D. Leslie.
"The Fluid-Compensated Cement Bond Log", by T. H. Nayfeh, W. B. Whellis, Jr., H. D. Leslie.
SPE 16207 "Coupling and Attenuation: A New Measurement Pair in Cement Bond Logging", by: H. D. Leslie, J. de Selliers, and D. J. Pittman.

Primary Examiner—Nelson Moskowitz
Attorney, Agent, or Firm—Henry N. Garrana; John H. Bouchard

[57] ABSTRACT

Acoustical coupling is proposed as a means of determining the presence and acoustical impedance of materials behind casing in cementation evaluation. Expressions for computing coupling and attenuation in multi-receiver/transmitter logging systems are analyzed in an exponential model for the spatial decay of elastic wave energy propagating axially along the casing. Amplitude change between transmitter(s) and receiver(s) is separated into a change dependent on coupling into and out of the casing wave, as well as a change related to attenuation along the casing. Coupling which is dependent on geometrical factors such as casing size and thickness, and on distribution and mechanical properties of the material outside the casing, shows principally the mechanical impedance of the material outside. Significantly, the bonding of this material to the casing is not a dominant factor for the coupling. Thus an estimation of cement strength may be made even in the presence of microannulus.

17 Claims, 4 Drawing Sheets

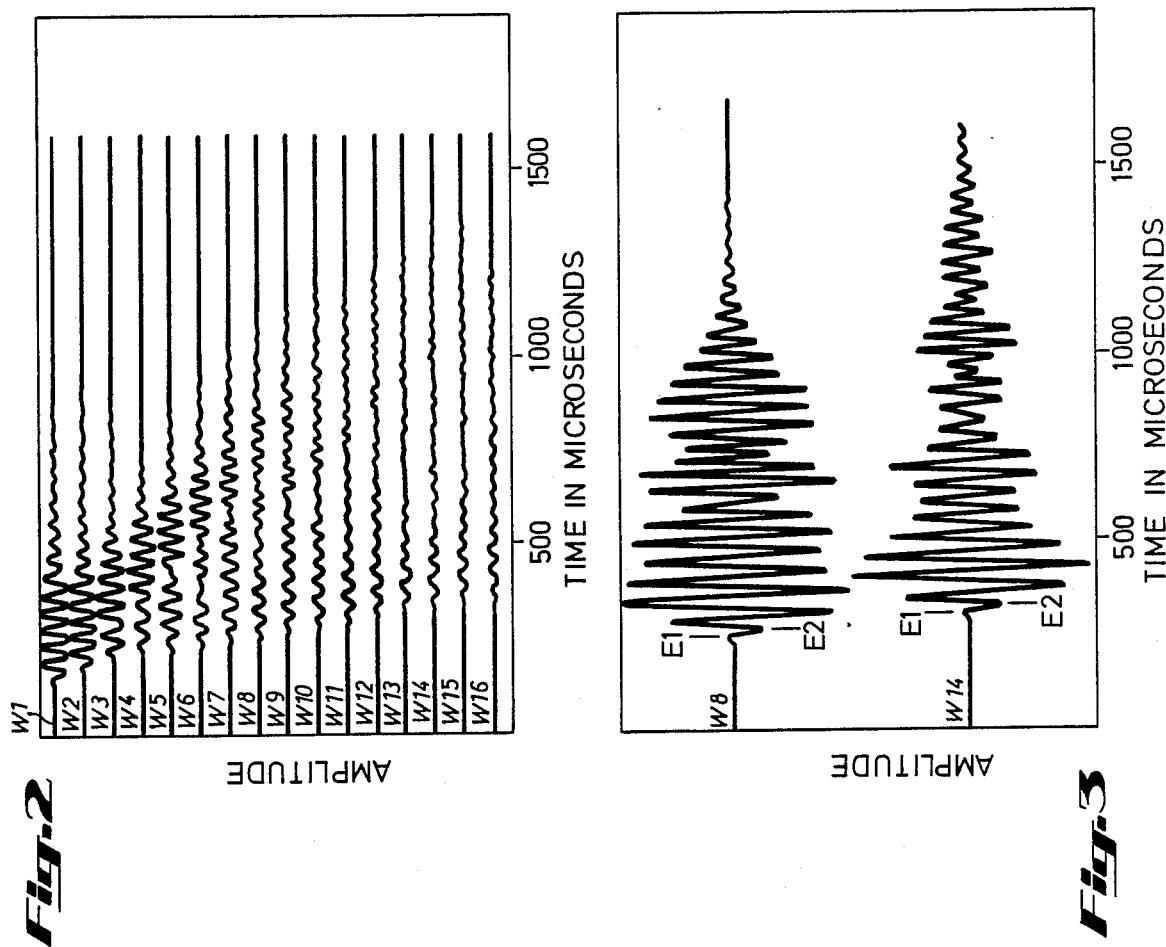
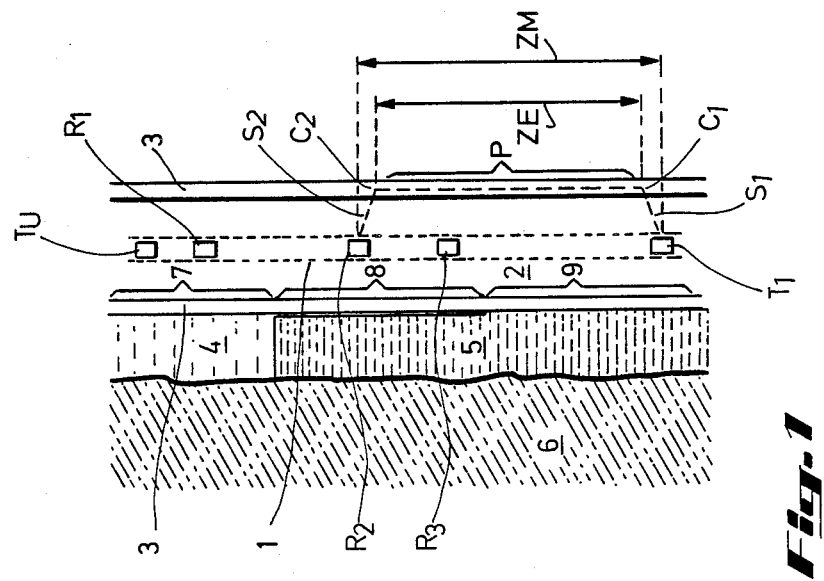

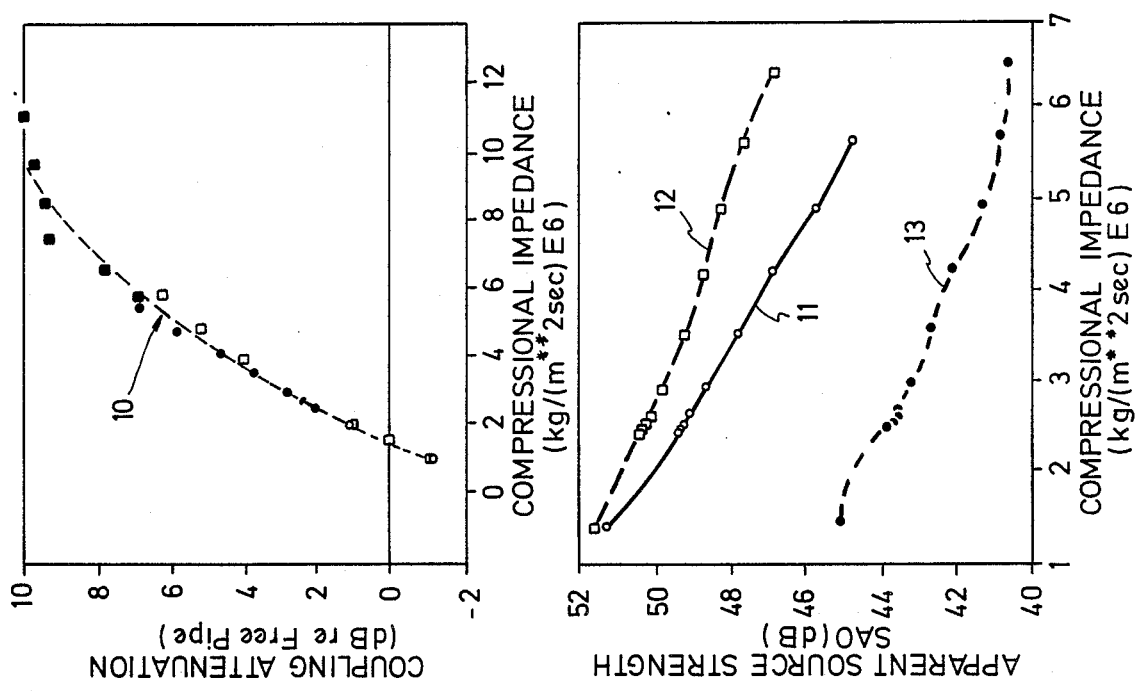
Fig. 5
Fig. 6
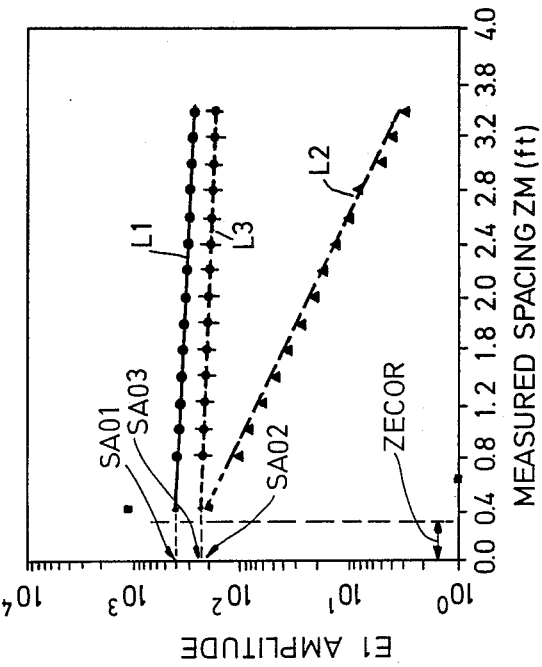
Fig. 4

METHOD FOR CEMENTATION EVALUATION USING ACOUSTICAL COUPLING AND ATTENUATION

BACKGROUND OF THE INVENTION

The present invention relates to a method for determining material characteristics in a borehole, being more particularly directed to a method for determining the presence and properties of materials behind or outside casing by acoustic wave measurements.

For many years acoustic logging has been used in cased wells for the purpose of determining the quality of the casing's cementation. The principle consisted of interpreting the amplitude of an acoustic signal received at some spacing from a transmitter in the borehole fluid. Improvements on this technique included using an array of transducers and thus deriving the attenuation rate of the signal along a defined length of casing. This attenuation rate is primarily a function of the mechanical properties of the cement that is bonded to the casing over that length.

The present invention is an improvement over previous acoustic logging with the two primary innovations in the present invention being concerned with:

1. The amplitude of the received acoustic signal being separated into two components: (i) a part due to the coupling of the acoustic energy between the wave in the borehole fluid and the wave propagating axially along the casing, and (ii) a part due to the attenuation of the wave propagating along the casing.

2. The part due to coupling being not only a function of the casing and of the borehole fluid, but also being useful to determine mechanical properties of the material outside the casing independently of its bond to the casing. From these properties, micro- and macro- annulus can be differentiated from free pipe or well bonded pipe.

In background, the "casing wave" measured in classical acoustical cement bond logging is a pressure wave reradiated back into the borehole fluid and there to a receiving acoustic transducer on the well logging instrument by an elastic wave passing axially along the steel casing. This elastic wave propagates as a Lamb mode of the thin steel cylinder. It is itself typically excited in the casing by a pressure wave emanating from a transmitting acoustic transducer in the well logging instrument. Prior industry practice has been to measure either amplitude of the casing wave, or to determine its spatial attenuation rate by taking amplitude measurements at different transmitter-receiver spacings.

Cement bond logs have traditionally been made by measuring the amplitude of the 1st significant acoustic arrival, generally referred to as the "E1" peak of the transient casing wave. This and other wavefronts are sensed by a receiving transducer separated from an impulsive acoustic transmitter by a preselected distance, such as 3.0 ft., along the axis of the casing. In some measurement techniques peaks other than E1 and/or spacings other than 3.0 ft. are chosen. Additionally, in some bond log data presentations, amplitude reductions relative to the amplitude measured at a single receiver in the "free", water backed, casing condition are converted to a pseudo-attenuation rate measurement.

An advantage of the present invention is the recognition that the amplitude reduction between transmitter and receiver depends not only on attenuation losses due to axial propagation along the casing, but also on the efficiency of acoustical coupling into and out of the casing wave. For single spacing measurement systems, for example one transmitter and one receiver, it is not possible to separate effectively these independent contributions to amplitude decrement. Amplitude reduction from all sources has often, mistakenly, been treated together and considered to be due to propagation along the casing. When additional casing wave amplitude controlling factors have been recognized they have not included the mechanical properties of the material outside and adjacent to the casing. Rather, properties of the materials outside the casing have been considered to control only the magnitude of the propagation attenuation rate, referred to also as the attenuation coefficient.

Recently, multireceiver cement bond tools have been introduced which are capable of measuring casing wave peak heights at more than a single transmitter-receiver spacing. One such tool is the Cement Bond Tool (CBT) produced by the instant assignee. Multispacing data provides a more complete description of the casing wave amplitude decay versus distance, and provides information necessary to determine the spatial attenuation rate itself. In the U.S. patent application Ser. No. 394,395, now Pat. No. 4,757,479, issued July 12, 1988 entitled "Method and Apparatus for Cement Bond Logging", filed July 1, 1982 and assigned commonly, incorporated by reference, a means of computing the spatial attenuation rate is disclosed along with appropriate apparatus in which factors affecting peak acoustic amplitudes other than the attenuation rate are cancelled out. By this means a compensated attenuation rate measurement is made which is independent of differences or changes in transmitter power outputs and receiver sensitivities and also is relatively independent of environmental factors such as borehole fluid properties.

Measurement techniques using multiple spacings are thus capable both of determining true attenuation rates and of separating them from other variations of amplitude, which are not associated with axial propagation along the casing. No successful attempt has previously been made, however, to exploit these capabilities and make use of that part of the amplitude variation which is not directly due to attenuation along the casing. Factors which will affect the absolute amplitude of the received casing wave signal have been reported as including only "environmental factors" such as borehole fluid properties, and the temperature or pressure characteristics of the measuring apparatus, not the properties of material outside the casing.

A particularly important shortcoming of previous cement evaluation logging systems which measure and rely only on the attenuation rate measurement is that this measurement is strongly affected by the microannulus which often appears between casing and the solid cement column after the cement has set up or solidified. These microseparations may occur either within the cement sheath itself, or at the interfaces of the cement column with the steel casing or formation. They may result from several factors including expansion and/or contraction of the casing due to either temperature or pressure cycles or borehole fluid changes or shock and vibration occurring during the well completion process, or to shrinkage of the cement itself. Often these microseparations are small enough that the permeability of the annulus is not significantly modified, and the hydraulic seal offered by the cement column not impaired. Microannuli do, however, severely reduce the acoustic attenuation rate measured by tools which determine the attenuation rate, and they cause the received amplitude to increase for tools which measure the peak amplitude only. Those measurements are thus not reliable measurements for use in estimating the hydraulic seal.

In the practice of the present invention, amplitude change between transmitter and receiver is separated into a change dependent on coupling into and out of the casing wave, as well as a change related to attenuation along the casing. Coupling is therefore an important amplitude controlling mechanism which depends on the properties of the material outside of the casing, but in functionally different ways than the attenuation. In particular, it has been found that the mechanical bonding between the casing and the cement sheath is not a dominant factor in the coupling.

Coupling magnitude additionally appears to be controlled largely by the compressional impedance of the material backing the casing and to a lesser degree by that material's Poisson ratio. Attenuation rate, on the other hand, is controlled mainly by the shear wave speed of the material which is bonded to the casing and thus is sensitive to the Poisson ratio as well as the magnitude of the compressional impedance. As another functional difference, coupling is controlled by the distribution of solid material in the annulus, that is, the percentage of casing surface area backed by cement within the investigation region of the coupling measurement, while attenuation is controlled by the percentage of surface area bonded to the cement.

The signals corresponding to coupling and attenuation rate thus respond differently to mechanical properties and geometrical configurations of the material behind the casing. Measurement of both coupling and attenuation allows determination of the presence of microannulus and estimation of average mechanical properties of material behind casing at each depth.

SUMMARY OF THE INVENTION

It is therefore an object of the present invention to provide a novel method for determining the presence of materials behind the casing in a borehole.

Another object is to provide a method for acoustically determining properties of the materials outside of such casing.

A further object is to provide a measure of cement quality in the presence of microannulus.

A still further object is to provide a method of determining the existence and width of microannulus gap between casing and cement.

Other and further objectives will be explained hereinafter and are particularly delineated in the appended claims.

In summary, however, from one of its broad aspects, the invention contemplates a method of determining properties of material behind casing in a wellbore comprising transmitting acoustic signals into a borehole; receiving at least two of said acoustic signals in said wellbore, each of said signals corresponding to different transmitter/receiver spacings; combining said acoustic signals to produce a compensated attenuation rate signal and a coupling attenuation signal; and determining the properties of the material behind the casing from measurements of the attenuation and coupling signals.

Preferred details are hereinafter more particularly disclosed.

BRIEF DESCRIPTION OF THE DRAWINGS

The invention will now be described with reference to the accompanyng drawings, in which:

FIG. 1 is a schematic representation of an acoustic logging tool useful under the present invention.

FIG. 2 shows a typical set of waveforms which might be acquired by another useful acoustic logging tool with sixteen transmitter to receiver spacings.

FIG. 3 shows portions of two received acoustical waveforms which may be used to determine the amplitude of the casing wave signal.

FIG. 4 shows a relation between casing wave amplitude and transmitter to receiver spacing for three different conditions.

FIG. 5 shows a relation between coupling reduction and outer material compressional impedance for a particular casing.

FIG. 6 shows a relation between coupling reduction and outer material compressional impedance for three casings with different combinations of outer diameter and wall thickness.

DETAILED DESCRIPTION OF THE PREFERRED EMBODIMENT

Figure 7:
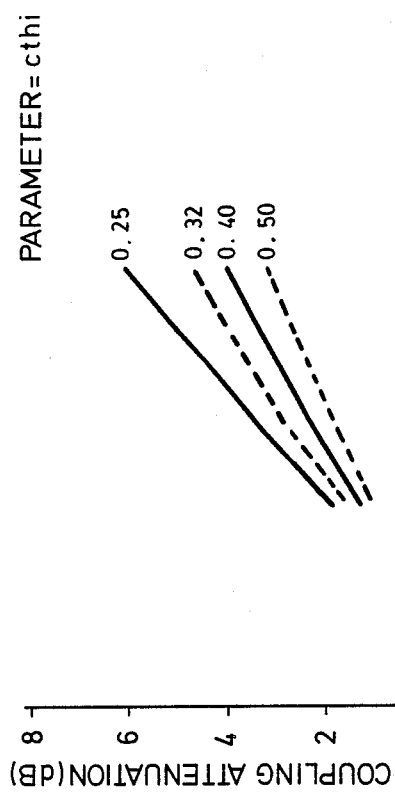
FIG. 7 shows a relation between coupling reduction and casing wall thickness for casing of a particular outer diameter, for outer materials of different compressional impedance.

Laboratory measurements and numerical simulation have shown that for thick cement sheaths surrounding oilfield casing, and for transmitter to receiver spacings large enough so that the casing wave is the first arrival, amplitude decay is exponentially dependent on spacing. The following exponential attenuation model is appropriate:

$$SA(ZM) = SAO \exp(-ATT * ZE) \qquad (1)$$

where:
- SA(ZM)—is the received peak amplitude in millivolts at spacing ZM
- SAO—is a "zero effective spacing" casing wave amplitude. SAO is the apparent source strength, depending on the coupling efficiency into and out of the casing wave in the vicinity of the transducers as well as environmental factors, measurement system sensitivities, and casing size.

ATT—is the propagation attenuation rate, also called the attenuation coefficient, along the casing in nepers per unit length.

ZM—is the transmitter to receiver spacing measured from midpoint of transmitter to midpoint of receiver.

ZE—is the effective acoustic spacing. It is the length of that portion of the path of energy (in the first peaks of the casing arrival) which travels along the casing between transmitter and receiver separated by spacing ZM.

Referring now to FIG. 1 there is shown an arrangement of acoustical transducers on a measurement instrument or tool such as a Cement Bond Tool (CBT) 1. The CBT 1 comprises two transmitters Tu and Tl and three receivers R1, R2, and R3. Four different transmitter to receiver spacings are available with this tool since the spacings between Tu and R1, R2, and R3 are 0.925 ft., 2.525 ft., and 3.525 ft. respectively, while the spacing between Tl and R1, R2, and R3 are 5.125 ft., 3.525 ft., and 2.525 ft. respectively. Each transmitter in turn emits a pressure pulse which propagates outward to the casing where some of its energy couples into modes of vibration of the casing. This casing wave energy propagates along the casing, attenuating as it radiates energy outward to the material behind the casing and inward into the wellbore fluid. In FIG. 1 rays are shown representing that portion of the energy which follows the least time path between transmitter T1 and receiver R2, contributing to the first arrival peak amplitudes at that particular receiver.

Sound leaves transmitter T1 and impinges on the casing wall 3 after suffering spreading and attenuation losses in the fluid, the losses being represented collectively in the figure as S1. Upon impinging on the casing some of this sound is converted into energy travelling in the "casing wave". Conversion efficiency is represented in FIG. 1 as C1. Additional losses associated with propagation attenuation along the casing are represented as P. The energy in the first few arches of the casing arrival is modelled as propagating over the effective path ZE along the casing when transmitter T1 and receiver R2 are separated by distance ZM measured from midpoint to midpoint of transducers. The propagating casing wave couples energy back into the borehole fluid continuously along the casing and in particular opposite the receiving transducer R2. This coupling is designated as C2. Attenuation losses occur again in the fluid near the receiving transducer as well as focusing of the wave on to the receiver R2. The net transfer function from the casing back to the receiving transducer R2 is designated S2. Similar ray paths may be depicted for other transmitter-receiver pairs.

In FIG. 1 several possible conditions are shown for the annulus between casing 3 and formation 6. This annulus may be filled with a fluid 4 such as water seen at location 7, or by a solid such as cement 5 which is bonded to the casing at location 9. Another commonly encountered condition is when cement fills the annulus except for a thin gap, referred to as a microannulus as at location 8. The cement is thus not bonded to the casing at either 7 or 8. Yet another commonly encountered condition is when cement fills part of the annulus and is bonded to the casing but a portion of the casing is backed entirely by a thick fluid layer. This condition is referred to as channelling.

FIG. 2 shows a typical set of waveforms labelled W1–W16 which might be acquired by another bond logging tool which has one transmitter, sixteen receivers, and transmitter-receiver spacing increasing in 0.2 ft. increments from 0.4 ft. to 3.4 ft. These particular waveforms were obtained from computer simulation using the real axis integration method (RAI) which is discussed in 2. Tsang, L. and Radar, D., "Numerical Evaluation of Transient Acoustic Waveform Due to a Point Source in a Fluid-Filled Borehole", Geophysics Vol. 4, p 1706–1720, 1979. The CBT tool would provide a similar result with, however, only six waveforms at the four preselected spacings.

The invention therefore contemplates the use of at least two signals that we used to provide the acoustic coupling and attenuation values. These signals may be created using one transmitter and at least two receivers or two transmitters and at least one receiver. Obviously multiple transmitter and receiver arrays and multiple frequencies are contemplated.

FIG. 3 shows a more detailed example of waveforms W9 and W14 of FIG. 2. A determination of casing wave amplitude is made by measuring the peak height of the first significant arch in the wavetrain. Casing wave amplitudes will be determined for each of at least two waveforms in order to compute propagation attenuation rate and coupling as shown in the preferred embodiment of proposed measurement.

In FIG. 3 W9 is the waveform which might be received at a spacing of ZM equals 2 ft. and W14 is the waveform which might be received at a spacing of ZM=3 ft. E1 is the peak amplitude of the first significant arch in each waveform which will be measured to determine the casing wave amplitude. E2 is the peak amplitude of the second arch which alternatively might be measured to determine the casing wave amplitude. Peak or root mean squared amplitudes of other arches or a combination of arches could also be used to determine the casing wave amplitude.

FIG. 4 shows the relation between casing wave amplitude and transmitter receiver spacing for the previously described 16 receiver tool under 3 different conditions of a 4.5 in. outer diameter (o.d.), 0.29 in. thick casing. For curve L1, or condition 1, the casing is backed with water as shown in FIG. 1 at 7. For curve L2, or condition 2, the casing is backed by and totally bonded to a solid material such as strong cement as shown in FIG. 1 at 9. For curve L3, or condition 3, the casing is backed by but unbonded to that same solid material, as by microannulus existing between casing and strong cement as shown in FIG. 1 at 8.

The points designated on curve L1 in FIG. 4 are the E1 amplitude measurements from the waveforms shown in FIG. 2, corresponding to condition 1 as shown in FIG. 1 at 7. Points designated on curve L2 in FIG. 4 are the amplitude measurements E1 from 16 waveforms under conditions 2 similar to that shown in FIG. 1 at 9. Points designated on curve L3 in FIG. 4 are the amplitude measurements E1 from 16 waveforms under the condition 3 similar to that shown in FIG. 1 at 8. The curves L1, L2, and L3 themselves are best fit lines to a subset of the 16 amplitude measurements in each condition. In particular they are the least squares fit to the amplitudes for receivers with measured spacings greater than 0.6 ft. using equations 2 and 3 as explained below.

In FIG. 4, with amplitude plotted on a logarithmic scale and measured spacing on a linear scale, the slope of a straight line such as curve L1 or L2 or L3 drawn through the data points is the spatial attenuation rate, of the propagating casing wave under the particular conditions. The ordinate of the intercept of that straight line with the vertical "effective spacing" equals zero line is the apparent source strength, SAO under the particular conditions. Effective spacing is defined below. In FIG. 4 apparent source strength for condition 1 is indicated on the ordinate, the E1 amplitude axis, as SAO1. Apparent source strengths for conditions 2 and 3 equal each other and are indicated as SAO2 and SAO3 respectively.

The effective acoustic spacing is not the same as the transmitter-receiver spacing since among other things the sound energy contributing to the first peaks of the casing wave is not expected to travel outward from the transmitter and inward to the receiver exactly perpendicular to the casing wall. For energy contributions to the casing arrival which enter at an inclined angle, such as the critical angle for water and steel, the effective spacing ZE will be slightly less than the transmitter receiver spacing ZM, as indicated in FIG. 1.

The concept of effective spacing can be further clarified and refined by referring to FIG. 4. The effective spacing reduction, ZECOR, is defined as that measured spacing ZM at which there is intersection of the log(amplitude) versus measured spacing line for bonded cement backed pipe (curve L2) and the log(amplitude) versus measured spacing line for unbonded, cement backed pipe (curve L3). The effective spacing reduction can be determined as by experimentation and computer simulation. Effective spacing ZE is then calculated as measured spacing ZM minus effective spacing reduction ZECOR. Measured spacing itself may depend on definitions such as measurement from center point of transmitter to center point of receiver.

By means of the above definition of effective spacing the apparent source strength computed in conditions of casing totally backed and bonded to cement is caused to be equal to that computed in conditions of a casing totally backed by but totally unbonded to such cement. Any dependence of actual coupling on bonding condition is thus removed. Simulations have in fact shown that the value of ZECOR defined above is slightly dependent on the mechanical properties of the cement, and thus to the value of attenuation for the totally backed and bonded casing. By using a constant value for ZECOR the dependence of computed coupling attenuation on bonding may be removed on the average.

Previously, for single spacing measurement systems, the "zero spacing amplitude", SAO, in equation 1 was assumed known. Cement bond tools are normally calibrated by placing them in a standard water filled, air backed, thin walled metal cylinder at prescribed temperature and pressure and adjusting the tool's selected peak amplitude reading to a preset value. The SAO amplitude for water filled and water backed casing is then known for a variety of oilfield casing pipe sizes and pipe weights. Both casing diameter and wall thickness are important parameters which determine the received peak amplitude for both fluid backed and cement backed pipe.

For multireceiver measurement systems both the attenuation coefficient and the casing wave apparent source strength SAO can be determined from the measured peak heights, Ai. For an N receiver system the linear least squares solution for SAO and ATT can be written $$SAO = \exp((D1*C22 - D2*C12/DET) \quad (2)$$

$$ATT = -(C11*D2 - C21*D1)/DET \quad (3)$$

where
SAO is the apparent source strength
ATT is the attenuation coefficient in nepers/unit length
SAi is the amplitude at receiver i
ZEi is effective receiver spacing i
C11 = N, the number of receivers
C12 = sum ZEi, i = 1,N
C21 = sum ZEi, i = 1,N
C22 = sum (ZEi)**2, i = 1,N
D1 = sum (ln SAi), i = 1,N
D2 = sum (ZEi*ln(SAi))
DET = C11*C22 - C21*C12

For two receiver systems the solution be written $$SAO = SA1 * 10**(ZE1 * PAR / 20.) \quad (4)$$

$$PAR = (20. / (ZE2 - ZE1)) * LOG10(SA1/SA2) \quad (5)$$

where
PAR is the propagation attenuation rate along the casing in units of decibels/ft., related to the attenuation coefficient as $$PAR = ATT * 20. / Ln(10)$$

SA1 is the peak amplitude at measured spacing ZM1
SA2 is the peak amplitude at measured spacing ZM2
ZE1 is the effective pathlength along the casing between transmitter and receiver separated by measured spacing ZM1
ZE2 is the effective pathlength along the casing between transmitter and receiver separated by measured spacing ZM2

The apparent source strength term SAO in equations 1, 2 and 4 will depend on the actual power output of the transmitting transducer and on the receiver sensitivity, both of which may be functions of temperature and pressure. Additionally, the measured pressure level will depend on the attenuation of the pressure wave over the pathlength in the fluid, to and from the casing wall and on the acoustic impedance of the borehole fluid. Finally, the apparent source strength will depend on the coupling between emitted and received pressure waves in the fluid and the casing ("Lamb") wave which will propagate along the casing. That is, it will depend on coupling between the emitted pressure wave and the casing wave as the mode is set up near the transmitter, and on the coupling between the casing wave arriving opposite the receiving transducer and the pressure wave in the fluid which is actually received.

Apparent source strength SAO is thus seen to depend on the measuring system characteristics, environmental factors, and coupling efficiency. In order to extract a measurement of coupling efficiency itself two approaches may be taken.

Ideally, values of factors affecting apparent source strength such as temperature, pressure, and borehole fluid properties will be available each time apparent source strength is computed. Measuring system sensitivities to these factors will also be known for the measuring tool in use and corrections will then be made to all amplitudes SAi used for computing SAO and ATT.

This is equivalent to adjusting the measuring system borehole environment to some standard condition, and also correcting for instrumentation errors such as transducer sensitivity changes and electronics errors. After this correction, the remaining variations of apparent source strength are assumed to be dependent only on variations of coupling from the standard conditions. Standard conditions might, for example, be standard laboratory conditions of 500 psi, 25 degrees C., with water both inside and outside a casing of the diameter and thickness being considered in the well. These would be considered standard "free pipe" conditions. When apparent source strength is computed from amplitudes adjusted for standard conditions a suitable coupling efficiency can be written:

$$CRST = SAOC(d) / SAOst \qquad (6)$$

where
CRST is coupling efficiency relative to coupling in standard conditions.
SAOC(d) is apparent source strength computed at depth d in the well from amplitudes corrected for instrumentation errors or drift and for environmental effects such as borehole fluid properties.
SAOst is apparent source strength for this casing size and thickness under standard conditions.

A second method of extracting a measurement of coupling efficiency is to compare the apparent source strength SAO(dref) computed at reference depth dref to the apparent source strength SAO(d) computed at some other depth d where all factors affecting apparent source strength except coupling efficiency are known to be the same. Temperature pressure and borehole fluid properties are, generally, slowly varying and can then be approximated as constant over typical logging intervals. Relative apparent source strength is determined and assumed to be equal to relative coupling. That is:

$$CREL = SAO(d) / SAO(dref) \qquad (7)$$

where
CREL is coupling efficiency relative to the reference condition
SAO(d) is the apparent source strength at depth d computed from amplitudes which have not been corrected to account for nonstandard environment.
SAO(dref) is apparent source strength computed at reference depth dref in the well computed from amplitudes which have not been corrected to account for nonstandard environment.

Local knowledge may allow a choice of dref such that the material behind pipe has about the same compressional impedance as the standard reference material, water. SAO(dref) is then apparent source strength under downhole free pipe conditions. Coupling will be determined relative to the reference downhole conditions.

The CBT logging tool measures receiver signals SA1 through SA6, in mV, from 6 transmitter-receiver pairs. Referring to FIG. 1 the amplitudes SAi are associated with the following transmitter to receiver pairs: SA1 with (Tu,R3), SA2 with (Tu,R2), SA3 with (T1,R2), SA4 with (T1,R3), SA5 with (T1,R1), and SA6 with (Tu,R1). After these measurements SAi are calibrated, i.e. corrected for measurement system errors and environmental factors, they are called SA1C through SA6C. The distance measured from the center of the transmitter to the center of the receiver is called ZM1 through ZM6 (in feet).

Therefore equation (1) can rewritten as:

$$SAiC = SAOst * 10 ** ((-PAR*ZEi - CAT)/20) \qquad (8)$$

where,
SAiC = the calibrated amplitude for transmitter-receiver pair i
SAOst = amplitude in water backed pipe (free pipe) for an effective spacing of 0 feet (in mV).
PAR = Propagation Attenuation Rate (in dB/ft)

$ZEi$ = effective spacing in feet for the measurement "i"
= distance on which the attenuation from propagation along the casing actually applies.
= $ZMi - ZECOR$ (correction for effective spacing).

and

CAT = Coupling Attenuation in dB, i.e. coupling referred to coupling in water backed pipe under standard conditions. Under standard conditions CAT = 0.

Noting that:

$$CAT = -20. * \log(CRST) \qquad (9)$$

And defining:

$$ATOst = 20 * \log(SAOst) \text{ (in dB)} \qquad (10)$$

The magnitude of the quantity in inner brackets in equation 8 is the total attenuation which is seen to result from "coupling attenuation" and "propagation attenuation".

Under the assumption that the measurements are made in a medium which is homogeneous over the tool length a simplified form of the equations for determining coupling attenuation and propagation attenuation rate may be employed. SAOst (ATOst), ZMi and ZECOR (ZEi) are parameters, assumed here to be known.

From any two transmitter-receiver pairs "a" and "b", we can compute:

$$PAR = (20 * \log(SAaC / SAbC)) / (ZMb - ZMa) \qquad (11)$$
$$CAT = (20*ZEb*\log(SAaC) - 20*ZEa*\log(SAbC)) / (ZEa - ZEb) + ATOst \qquad (12)$$

Thusly, unlike for PAR, the computation of CAT requires prior knowledge of the parameters ZEi and ATOst.

If corrections cannot be made to amplitudes SAi in order to determine calibrated amplitude measurements SAiC, an estimate of PAR and CAT can still be made from equations 11 and 12. In this case ATOst in equation 12 will be replaced by AT0(dref) which is established under downhole conditions using equation 8 with CAT assumed equal to zero. In equations 8, 11, and 12 SAiC will be replaced by measured amplitudes SAi.

Considering the CBT transducer configuration as illustrated and frequently used in FIG. 1, for several reasons, 2 spacings appear to be most useful for making the CAT computation:
the "short" spacing measurement (SA6, ZM6 = 0.925')

the "near" spacing measurements (SA2 and SA4, ZM2=ZM4=2.525').

The physically reasonable range of true spacings for exponential decay is limited through casing diameter and fluid sound speed for the short spacings, and through signal to noise ratio at the longer spacings.

At short spacings the direct fluid arrival will precede the casing arrival. In fast fluids and for larger casing sizes the problem is most severe. A spacing of at least 0.925 ft. will allow the casing arrival to precede the direct fluid arrival in fluids normally encountered in oilfield well logging if the casing size is 7.0 in. or smaller, and if transducer sizes are about 2 in. o.d. If transducers are larger and thus closer to the steel casing the minimum spacing can be reduced slightly.

At long spacings "road noise" will contribute to the measured casing wave amplitude and distort the normal exponential decay versus spacing. A spacing such as 3.525 ft. appears to be the upper limit given presently available cement bond logging hardware. Beyond this spacing, attenuations greater than about 12 dB/ft. will not be accurately measured due to noise problems.

Preliminary numerical simulations appear to indicate that for cement sheaths of finite thickness, amplitude decay may depart slightly from exponential decay when interferences occur between the casing arrival and additional energy, such additional energy being reflected from the outer interface between cement sheath and formation. These simulations have shown that for a variety of outer material properties and cement layer properties, the region of nonexponential decay is confined to shorter spacings. The extent of the perturbation of the exponential decay by the reflected energy will depend also on the sound speed in the cement sheath and the impedance contrast at the cement outer interface.

The CBT acquisition software presently makes one acquisition of measurements from all transmitter-receiver pairs every 6 in., and assigns "measurement points" to the midpoint between transmitter and receiver for the amplitude measurement from each particular transducer pair. All measurements are then memorized so that the individual measurement points are aligned to a common reference measure point whose depth is then associated with the measured values on the cement bond log. For simplicity, indications between brackets refer to the depth offset of the individual memorized amplitude measurements (in feet) as referred to the reference measure point for the final coupling attenuation value. For example SA6(0) is the SA6 measurement made at the reference measure point where CAT is to be computed. SA2C(−1) is the calibrated SA2 measurement whose measurement point is 1 ft. below the reference measure point for the CAT computed value.

Lab measurements indicate that the Coupling Attenuation (CAT) for the CBT has a very fine vertical resolution. It is mainly influenced by the mechanical properties of the outer material in a 2 to 3 inch long section in front of both the transmitter and the receiver. The coupling attenuation measurement will then respond to coupling efficiency near each of the transducers used in its determination. The computation is therefore structured so that the computed coupling attenuation is more localized, and representative of the materials actually at the coupling attenuation measurement reference point. Further, by combining amplitude measurements taken at several depths, allowance is made for variation of material properties within the length of the well logging instrument. The material backing the casing need not then be homogeneous and the computed value of CAT will still be an accurate estimate of the localized coupling attenuation.

To comply with all the above constraints, two nearly equivalent base formulas, CAT1 and CAT2, are proposed for the computation of the coupling attenuation CAT ; one of them, or some combination of the two, may be used in the tool acquisition software, the final choice being made on practical considerations linked to the software environment.

The parameter ZECOR may be fixed in software as a function of casing size, and the parameter ATO selected by the field engineer depending on the well's conditions. The process for the calibration of SAi follows standard form in the art.

Therefore, the two algorithms are:

Algorithm 1

$$ANAT(0) = (ATO - 5*\log(SA2C(+0.5)*SA2C(0)*SA4C(+0.5)*SA4C(0)))/ ZE2 \quad (13)$$
$$= \text{averaged "near" spacing attenuation}$$
$$= PAR + CAT / ZE2$$

$$ASA1(0) = (ATO - 4*\log(SA6C(+1)*SA6C(+0.5)*SA6C(0)*SA6C(-0.5) \quad (14)$$
$$*SA6C(-1)))/ZE6$$
$$= \text{averaged "short" spacing attenuation \#1}$$
$$= PAR + CAT / ZE6$$

$$CAT1(0) = (ASA1(0) - ANAT(0)) * ZE2 * ZE6 / 1.6 \quad (15)$$

Algorithm 2

$$SNAT(0) = 5 * (\log((SA6(+1)*SA6(-1))**2 \quad (16)$$
$$/ (SA2(+0.5)*SA2(0)*SA4(+0.5)*$$
$$SA4(0)))) / 1.6$$
$$= \text{"near" to "short" propagation attenuation rate}$$
$$= PAR$$

$$ASA2(0) = (ATO - (10 * \log(SA6C(+0.5) * \quad (17)$$
$$SA6C(-0.5)) +$$
$$20 * 0.6 * \log(SA6C(0))) / 1.6) / ZE6$$
$$= \text{averaged "short" spacing attenuation \#2}$$
$$= PAR + CAT / ZE6$$
$$CAT2(0) = (ASA2(0) - SNAT(0)) * ZE6 \quad (18)$$

CAT1 and CAT2 are both estimates of the coupling attenuation CAT at the reference measure point.

Laboratory testing and numerical simulation results are now discussed to illustrate application of the coupling attenuation measurement. These results show that the coupling of energy into and out of the casing is dependent not only on the elastic properties and density of the casing and the borehole fluid, but also on the elastic properties and density of the material on the outside of the casing. The most important property of the material outside the casing is its compressional impedance. The actual mechanical bonding of this material to the casing is unimportant provided the material is close to the casing outer surface. Propagation attenuation rate of the casing arrival, on the other hand, is determined primarily by the bonding strength of the material outside of the casing. Bonding strength is determined by either chemical bond strength or mechanical/frictional bond strength and the shear modulus of the material which is bonded. Compressional modulus is of secondary importance. The outer material, such as cement, must be actually touching the casing outer surface, and strongly bonded to it for significant attenuation to occur. Internally pressurizing a casing often increases the shear bonding without changing the moduli of the outer material.

Coupling attenuation will be referred to also in the following discussion as apparent source strength reduction or AOred. Results of numerical simulation using RAI (reference 2) were made under the following conditions unless designated as otherwise: a centralized point source with 20 KHz center frequency, point receivers, and water as borehole fluid. The outer material was adjacent, but unbonded to the casing. A Poisson ratio of 0.315 has been used for all "standard cement" computations except where noted. Apparent source strength has been determined from equations 2 and 3 above, after peak amplitudes, SAi, were measured for all simulated waveforms. Where coupling attenuation is discussed the apparent source strength has been normalized by the apparent source strength found in the simulations for water backed pipe, yielding the relative coupling, CREL, and presented in dB as CAT or AOred.

FIG. 5 shows the trend line 10 of the coupling attenuation versus the compressional impedance of a variety of outer materials for a 5.5 in. o.d., 0.25 in. thick casing. Points near the trend line in FIG. 5 represent coupling attenuation values computed in separate simulations for which the properties of the unbonded material backing the casing were varied. These outer materials included fluids of varying densities and sound speeds, cements of different compressional impedances, and sandstones of varying porosities. In each of these simulations a set of 16 waveforms such as that shown in FIG. 2 was computed. Values of SAO were determined corresponding to SAO3 shown in FIG. 4, using a constant value of ZECOR for all simulated cases. Coupling attenuation is seen to increase as outer material compressional impedance increases.

Both experimental studies and numerical simulation have shown that the thickness and diameter of the casing are also important in determining the magnitude of the coupling and its sensitivity to the compressional impedance of the outer material. In FIG. 6 line 11 shows the trend of apparent source strength SAO in dB versus compressional impedance for the same casing used in FIG. 5 (5.5 in o.d., 0.25 in. thick). Line 12 shows the trend for a thicker casing (5.5 in. od., 0.4 in. thick) while line 13 shows the trend for a larger casing (9⅝ in. o.d., 0.25 in. thick). Points designated on the curves are the results from numerical simulation. No normalization of the apparent source strength has been made. Increasing the casing thickness, in this example, causes both water backed apparent source strength to be increased (at compressional impedance equal to 1.5) and sensitivity of apparent source strength to outer material impedance to be reduced. Greatest sensitivity of apparent source strength SAO to compressional impedance occurs in smaller, thinner casing.

Figure 8:
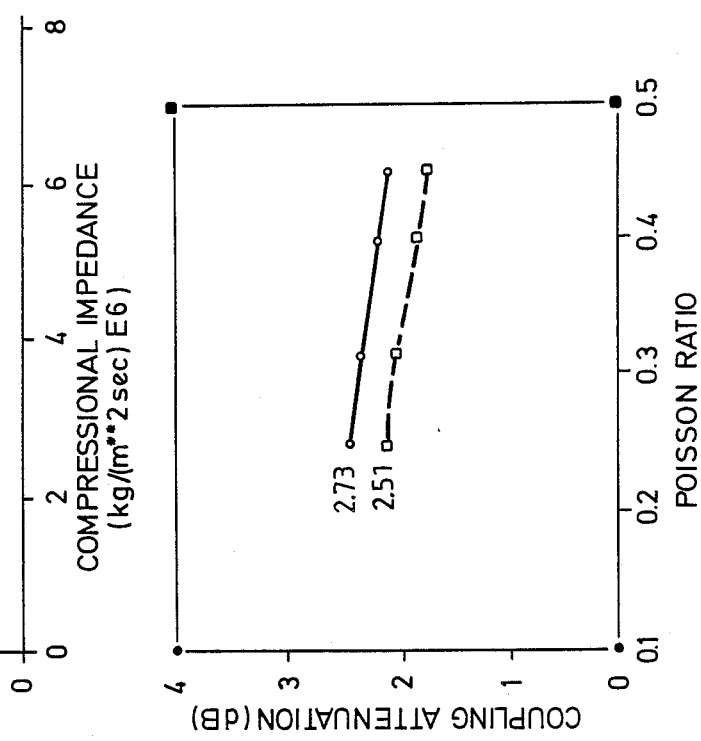
FIG. 8 similar to FIG. 7, shows the relation between coupling reduction and outer material compressional impedance for casing of a particular outer diameter for several different casing wall thicknesses.

FIG. 7 shows apparent source strength reduction AOred (coupling attenuation) from the water backed pipe value versus casing thickness for a particular casing size (7 in o.d.). Eight examples of outer material compressional impedance are charted. In FIG. 7 lines of constant compressional impedance are designated by the value of the compressional impedance in units of $(kg/(m^{**}2 \text{ sec.}) E6)$. FIG. 8 shows the same simulated data as in FIG. 7 with apparent source strength reduction AOred plotted versus the outer material compressional impedance for 4 different casing thicknesses of the 7 in o.d. casing. Lines of constant casing thickness are designated by the value of the thickness in inches. These figures will be discussed more with respect to a following example.

Figure 9:
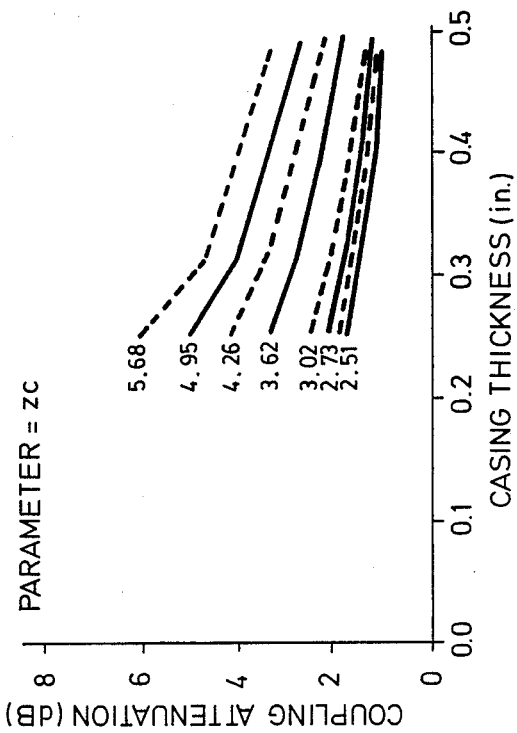
FIG. 9 shows a relation between coupling reduction and Poisson ratio of the material outside the casing for materials of several different compressional impedances.

The low sensitivity of coupling attenuation to Poisson's ratio (PR) of the solid material behind the casing is illustrated in FIG. 9, for a particular casing size (4.5 in. o.d.) and thickness (0.25 in.). This figure shows reduction in coupling relative to coupling for the water backed casing versus Poissons ratio in the reasonable range 0.45 to 0.25. Several curves are shown, each for a fixed value of compressional impedance which designates the curve and whose values are given in units of $(kg/(m^{**}2 \text{ sec.})E6)$. Sensitivity of AOred to compressional impedance is seen to be far greater than that to Poissons ratio.

Figures 10, 11, 12:
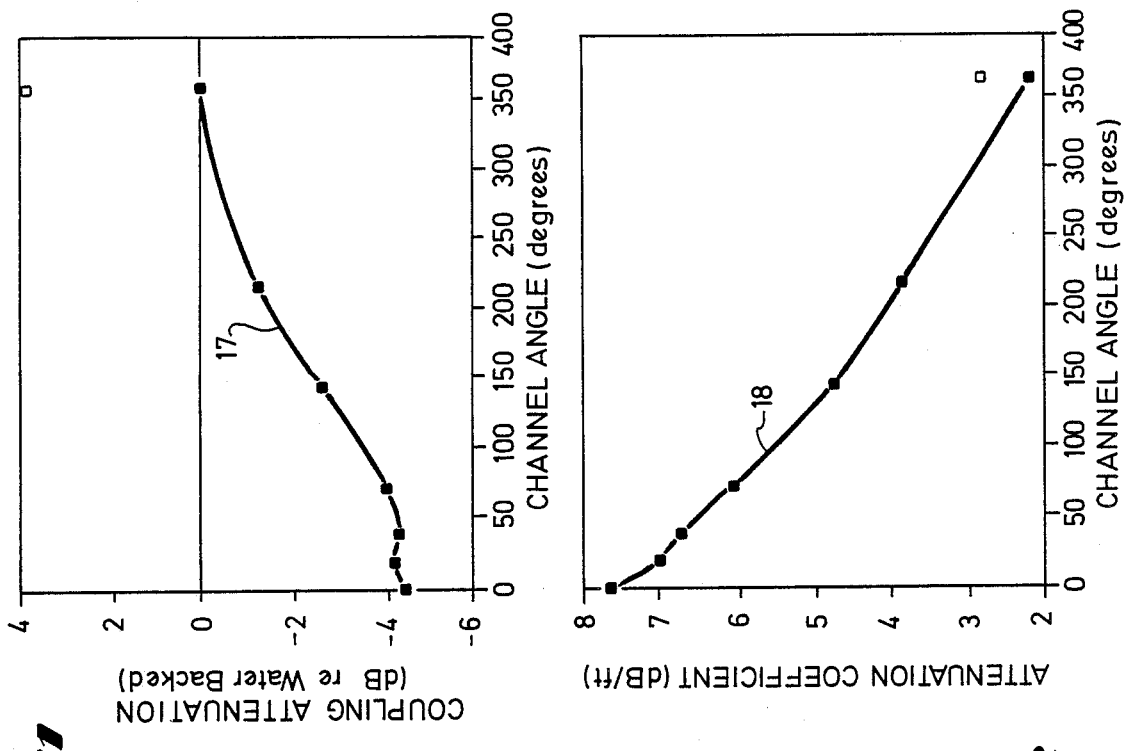
FIG. 10 shows a relation between coupling reduction and thickness of a thin water filled layer between casing outer surface and/inner surface of several materials with different compressional impedances.
FIG. 11 shows a relation between coupling reduction and the width of a water filled channel in the cement, oriented axially against the outside of the cemented casing.
FIG. 12 shows a relation between propagation attenuation rate and the width of a water filled channel in the cement, oriented axially against the outside of the cemented casing.

The degree of sensitivity of coupling attenuation to the width of a thin fluid filled gap between casing and cement is illustrated in FIG. 10. A thin water layer has been introduced in the examples between outer casing surface and inner cement surface for a casing which has a 5.5 in. o.d. and a 0.25 in. thickness. Results of simulations are shown for three different outer materials and plotted as Coupling attenuation versus the thickness of the thin water gap. For trend line 14 the outer material is cement of compressional impedance equal to 2.73 $(kg/(m^{**}2 \text{ sec.}) E6)$. For trend line 15 the outer material is cement of compressional impedance 3.01. For trend line 16 the outer material is cement of compressional impedance 4.25. For thicknesses of this water layer less than about 0.05 in., coupling attenuation is the same as that occurring for a bonded cement sheath of the same compressional impedance, or for an infinitesimally thick water gap. For water gap thickness greater than about 0.5 in. the coupling attenuation is approximately equal to that for an infinitely thick water gap. In the range of water gap thicknesses 0.05 in. to 0.5 in. the coupling attenuation gradually decreases from its bonded level to its water backed level.

The thickness of the thin water or gas filled layer between casing outer surface and cement or outer material inner surface is here in referred to as the macroannulus size. Normally in oil or gas wells the size of the gap resulting from cementing and completion operations is expected to be less than about 0.01 inches and is referred to as a microannulus. Coupling attenuation is thus insensitive to the presence of water filled microannulus for the microannulus sizes usually encountered in oil and gas wells.

The lower limit of 0.05 inches and the upper limit of 0.5 inches of the macroannulus size, for which the coupling attenuation in the present simulations shows a transition between solid backed and water backed response, are themselves dependent on the wavelength of compressional energy in the material constituting the macroannulus. These limits can be adjusted by changing the frequency content of the signal emitted by the well logging instrument. Increasing the frequency will push these transition thicknesses to smaller values. Therefore by varying the frequencies used in the well logging instrument the width of the microannulus gap can be estimated.

Azimuthal distribution of cement behind the casing in the vicinity of the transmitter and receiver is also important in controlling the magnitude of the acoustic coupling. Testing reveals that there is a slightly nonlinear relation between the width of an axial channel in the cement sheath and the level in dB of coupling attenuation observed at the frequencies tested. Coupling increases from the value it would have had in a totally cement backed pipe to the value it would have had in a totally water backed pipe, as a water filled channel angle increases from 0 deg. to 360 deg.. FIG. 11 shows this response for axial channels of 5 different Widths. Cases of 100% cement backed, 100% water backed, and 100% air backed have also been recorded. The cement used in the example given had a compressional impedance of about $2.83 * 10^{**}6$ kg/(m2*sec.), compared to $1.5 * 10^{**}6$ for water. Coupling attenuation decreased by about 4.5 dB going from cement backed to water backed pipe. Another 3.8 dB occurs from water backed to air backed pipe. In FIG. 11 trend line 17 shows the relation between coupling attenuation and width of the vertical water filled channels. Points designated on the line are the actual values of coupling attenuation computed using equations 2 and 3 from amplitudes measured at 24 spacings.

As is well known, the azimuthal distribution of cement behind the casing between transmitter and receiver is also important in controlling the magnitude of the propagation attenuation rate, PAR. Additionally there appears to be also a slightly nonlinear relation between the width of an axial channel in the cement sheath and the value of propagation attenuation rate in dB/ft observed at the frequencies of the example. The attenuation coefficient decreases nearly linearly from the value it would have in a totally cement backed pipe to the value it would have in a water backed pipe. FIG. 12 shows this response for the same example discussed above with regard to FIG. 11.

Vertical distribution of cement behind the casing in the vicinity of both the transmitter and receiver is also important in determining the magnitude of the acoustic coupling. Test have shown that the ability of the coupling measurement to resolve changes in compressional impedance behind casing can be quite sharp, on the order of the size of the transmitting and receiving transducers. This resolution will also depend on frequency of the transmitted acoustic pulse, the axial length of the transducers, and the diameter difference between casing and transducer.

In summary, it is apparent that the value of coupling attenuation computed in the manner described above depends directly on the compressional impedance of material outside the and on the distribution of that material in the annulus in the vicinity of the transmitting and receiving transducers. Coupling is weakly dependent on the Poisson ratio of the outer material. It is not affected by a water filled macroannulus of thickness up to about 0.1 inches for a sonic logging tool with center frequency around 20 kHz, and 3 dB bandwidth of 9 kHz as was used in the examples described above. For tools whose transmitters and receivers are not azimuthally directional (in a cylindrical coordinate system with axis along the axis of the casing), contributions to the measured peak amplitudes will be received from all azimuthal directions. The coupling attenuation will depend on the combination of cement presence and strength, and thus is a measure of the average compressional impedance.

Compressional impedance may be estimated from coupling by using charts of the type of FIG. 7. Charts of coupling may be constructed either from results of laboratory experimentation or numerical simulation for casing sizes of interest. The secondary dependence of coupling on Poisson ratio may be ignored and nominal values of 0.315 used to construct the chart as in FIGS. 7 and 8, or charts may be constructed using other presumed values of Poisson ratio. To use the chart shown in FIG. 7 coupling reduction (attenuation) relative to coupling in water backed pipe is computed from casing wave amplitude measurements using expressions such as equations 12, 15, or 18 given above. Computed coupling attenuation is then plotted versus casing thickness in FIG. 7 and the value of compressional impedance is determined by interpolating between closest lines of constant compressional impedance as will be explained in more detail in a following example.

Alternatively, charts such as that shown in FIG. 8 may be used. A line of constant casing thickness equal to that of the known actual casing thickness is created by interpolating between nearby lines of casing thickness already on the chart. A horizontal line is drawn through the vertical axis at a level corresponding to the computed coupling attenuation. Position is determined along this line at the intercept with the curve of constant actual casing thickness. Average compressional impedance of the outer material is read as the horizontal coordinate.

Compressive strength is a useful material property to determine since it has become an industry standard for characterizing oil well cements. From the relation between the coupling attenuation and the compressional impedance, and from relations such as those in reference 3 between compressional impedance and other mechanical properties (i.e. compressive strength) of cement, an apparent compressive strength of the material behind casing can be computed from the coupling attenuation.

Assuming the properties (compressional impedance) of the cement are known and constant, one can also compute a "cement index" (CI) from CAT, in addition to the usual "bond index" (BI) computed from PAR:

CI = CAT / CATMAX where
CI is the cement index
CAT is the computed value of coupling attenuation
CATMAX is the maximum value of coupling attenuation, the expected value for the particular cement and casing.

CATMAX can either be estimated from the log, or picked from a chart of Coupling Attenuation versus compressive strength of cement for the given casing. Under the above assumption, the Cement Index is a measure of the portion of the casing that is backed by cement. Results illustrated in FIG. 11 suggest that CI increases as the percentage of the pipe surface area backed by cement increases. CI equals zero when the pipe is backed by water and equals one when the pipe is backed entirely by cement of the expected strength.

A bond index which already is in use in the industry is computed as :

$$BI = (PAR - PARMIN) / (PARMAX - PARMIN)$$

where
- BI is the bond index
- PAR is the computed value of propagation attenuation rate
- PARMIN is the value of propagation attenuation rate expected for the free pipe condition of the particular casing
- PARMAX is the maximum value of propagation attenuation rate expected for the particular cement and casing.

Here also PARMIN and PARMAX may be determined from the log. Alternatively, PARMAX may be picked from a chart of propagation attenuation rate versus compressive strength of cement for the given casing and PARMIN may be picked from a chart of propagation attenuation rate in free pipe versus casing size and thickness.

This bond index is then a measurement of the portion of the casing that is bonded to the cement.

When the bond index is smaller than the cement index, it may be an indication that some of the cement in place is not bonded to the casing (micro- or macro-annulus). That is, generally when the coupling attenuation is high and the propagation attenuation is low, microannulus can be expected.

As indicated above apparent compressive strength may be computed from estimated compressional impedance. When this apparent compressive strength corresponds to that of the cement used in the zone of interest, the casing is likely to be fully backed by cement. If in such a zone the propagation attenuation rate is below that expected for a fully bonded casing, it is an indication of probable micro-or macro-annulus. If, on the other hand, the apparent compressive strength is less than that of the cement used, and the propagation attenuation rate is below that expected for a fully bonded casing, it is an indication that the cement is either channelled or weaker than expected, for instance because of mud contamination.

To illustrate the interpretations which may be made using coupling attenuation and propagation attenuation rate, consider the situation of a well containing 7.0 inch o.d., 23 lbs/ft. casing with nominal wall thickness of 0.317 inches, backed by cement of compressive strength approximately equal to 4000 psi, for which the compressional impedance is 4.95 (kg/(m**2 sec.) E6).

Initially, the value of apparent source strength must be determined for this pipe size by measuring peak heights of casing wave amplitudes acquired by the logging tool under reference conditions of water behind the casing. This may be done downhole in an area such as that shown in FIG. 1 at 7, or it may be done at the surface under standard conditions. Best estimates of coupling and attenuation will be obtained if all amplitudes SAiC are obtained with properly calibrated transducers, compensated for environmental changes.

Amplitudes obtained under free pipe conditions will plot along a line such as L1 in FIG. 4, for which the slope is the free pipe attenuation rate. A value of ZECOR for this pipe size of about 0.25 ft. will be used to correct all measured spacings to effective spacings. Depending on the tool configuration equations 2 and 3, or equations 11 and 12, or 15, or 18 can be used to compute values of propagation attenuation rate PAR and reference apparent source strength SAOst (and ATOst). If equation 12 or 15 or 18 is used CAT or CAT1 or CAT2 is set to zero and the equation solved for ATOst and equation 10 used to determine SAOst. If equation 2 is used SAOst=SAO. For this casing size we expect a free pipe propagation attenuation rate, PARMIN, of about 0.53 dB/ft.. Knowing the reference apparent source strength, SAOst (or ATOst), coupling attenuation may be determined in other intervals of the well.

In another interval of the well where the cement is bonded to the casing such as shown in FIG. 1 at 9, waveforms will again be received and peak amplitudes E1 measured. These peak amplitudes will fall along a straight line such as L2 in FIG. 4. A value of ZECOR of 0.25 ft. is again used to correct measured spacings. Then using equations 2 and 3 or equations 11 and 12 or 15 or 18 propagation attenuation rate and coupling attenuation are determined. Under bonded conditions, for this casing size and cement type, we expect PAR results should be equal to 10.34 dB/ft. and apparent source strength SAO to be such that CRST which is equal to SAO/SAOst equals 0.633, and CAT thus equals 3.97 dB.

In order to determine the average compressional impedance in this interval reference a chart of the type of FIG. 7 for the casing size of 7.0 inches. Locating the point CAT=3.97 dB, casing thickness=0.317 interpolate between closest lines of constant compressional impedance to determine that the compressional impedance equals 4.95.

Alternatively, enter a chart of the type of FIG. 8 for the casing size of 7.0 inches. Locating the point CAT=3.97 dB and move horizontally to a line of constant casing thickness of 0.317 which is determined by interpolating between nearest lines of constant thickness which are on the chart. Then move down to the abscissa to read the compressional impedance of 4.95.

If the cement occupies the entire annulus and is bonded in the zone as shown in FIG. 1 at 9, and if the cement has not been diluted during placement, and if the cement has solidified according to its design schedule, then this zone will be among the most well cemented zones in the well, among zones where that cement slurry was used. CAT measured in such a zone may then be used as CATMAX, and PAR measured in such a zone may be used as PARMAX.

Another choice of CATMAX may be made by repeating the operations explained above for determining the compressional impedance, but in reverse. That is, the design impedance of the slurry is used to enter charts of the type FIG. 8 on the abscissa with, for example, a value of cement compressional impedance equals 4.95. Proceeding vertically to a line of constant casing thickness of 0.317 which is determined by interpolating between lines of constant casing thickness which are on the chart, the expected maximum value of CAT (CATMAX) equal to 3.97 dB is read as the ordinate.

Once a value of CATMAX has been determined the value of cement index may be computed at all locations in the well. The cement index in the well cemented zones will have values approximately equal to one.

As a further example, consider another zone where a vertical mud filled channel occupies about 108 degrees, thirty percent of the annulus. From charts of the type of FIG. 11, which shows an experimentally observed relation between coupling attenuation and channel angle, it is expected that measured coupling attenuation, CAT, in this zone, and for this casing size, cement type, and channel width, will be about 3.09 dB. From other data, such as that shown in FIG. 12 of channel angle versus measured propagation attenuation rate, PAR, one expects that in this zone PAR will be about 7.58 dB/ft. Then one computes the cement index, CI, to be 3.09/3.97=0.78 and the bond index to be (7.58−0.53)/(10.34−0.53)=0.72. Since bond index is approximately equal to cement index and both are significantly less than one it is concluded that a channel is present.

As an additional example, consider another zone where cement occupies the entire annulus but is not bonded to the casing as shown in FIG. 1 at 8. In this case the measured attenuation rate will be about 0.6 dB/ft. and the measured coupling attenuation will be about 3.97 dB. One can compute the cement index, CI, to be 3.97/3.97=1., while the bond index is (0.6−0.53)/(10.34−0.53)=0.007. Since cement index is much larger than bond index one concludes that microannulus is present.

In summary, therefore, a new measurement has been proposed for cement bond logging. Acoustical coupling is identified as an important amplitude controlling mechanism which depends on properties of the material outside the casing and which can be separated from propagation attenuation when two or more transmitter to receiver signals, are present. This multiplicity of spacings may be achieved by using a 2 transmitter, 3 receiver tool similar to that shown in FIG. 1, or with an arbitrary array of transmitters and receivers, as noted previously in contemplation.

An exponential decay model is assumed for the casing arrival in the proposed algorithms to compute coupling and attenuation. This amplitude versus spacing dependence is in fact observed in modelling within a restricted transmitter to receiver spacing range, when the cement sheath thickness is large enough. Factors which perturb exponential decay include the direct fluid arrival, road and system noise, and reflected energy from the outer cement interface.

Previous cement bond logging techniques have required a careful calibration of transmitter and receiver in order to relate peak amplitude to cement strength. Multi-receiver/transmitter amplitude measurements, however, allow attenuation to be computed independent of transmitter and receiver sensitivities through the BHC principal documented in the "Method and Apparatus for Cement Bond Logging" referenced previously. Effective zero spacing amplitude SAO may also be computed without regard to system calibration and used as a "relative coupling" indicator. However, as such it will also depend on measuring system sensitivities to temperature and pressure, and on environmental factors such as impedance and Q of the borehole fluid, and on geometrical factors such as casing size, thickness and transducer design.

In order to relate coupling to cement impedance and distribution alone it is necessary to compensate for system sensitivities, and environmental and geometrical factors. This may be accomplished by normalizing coupling to the coupling observed either downhole in free pipe or in standard reference conditions. An additional compensation must then be made for any changes in factors between the zone of interest and the free pipe zone. Similarly, if surface calibration is performed, compensation must be performed to account for downhole environment.

Coupling has been found to depend predominantly on the compressional impedance of the material outside the pipe and its distribution in a thin vertical band opposite transmitter and receiver. An effective outer material impedance can be determined from coupling, which depends on both the cement impedance and distribution. If cement strength is known, this "cement index" can be computed from the calibrated coupling and the tabulated coupling reduction values appropriate for that cement strength and casing size.

This cement index is not strongly dependent on bonding and thus is less perturbed than attenuation derived "bond index" under conditions of a water filled microannulus being introduced between casing and cement. When coupling reduction and attenuation, or alternatively cement index and bond index, are compared the presence of a thin fluid or gas filled macroannulus between casing and cement may be deduced, for macroannulus thicknesses up to a critical size. The critical size can be adjusted by choosing the operating frequency of the cement bond logging tool.

Further modifications will also occur to these skilled in the art, and such are considered to fall within the spirit and scope of the invention as defined in the appended claims.

What is claimed is:

1. A method of determining the properties of a material disposed behind a casing in a wellbore, comprising:
    using a transmitter means adapted to be disposed in the wellbore within said casing, transmitting acoustic signals into said wellbore;
    using a receiver means adapted to be disposed in the wellbore within said casing, receiving at least two of said acoustic signals in said wellbore, each of said signals corresponding to different spacings between a transmitter of said transmitter means and a receiver of said receiver means;
    combining said acoustic signals and deriving from each of the acoustic signals a compensated attenuation rate signal representative of an attenuation of the received acoustic signal produced while propagating axially along said casing and a coupling signal representative of an attenuation of the received acoustic signal produced while propagating between the transmitter and said casing and between the receiver and said casing; and
    determining the properties of the material behind the casing from both the attenuation rate signal and the coupling signal associated with each of the received acoustic signals.

2. A method as claimed in claim 1 wherein one of the properties of the material disposed behind the casing determined during the determining step is the presence of material.

3. A method as claimed in claim 1 wherein one of the properties of the material disposed behind the casing determined during the determining step is an acoustical impedance of the material.

4. A method as claimed in claim 1 wherein one of the properties of the material disposed behind the casing determined during the determining step is a cement index of the material.

5. A method as claimed in claim 1 wherein one of the properties of the material disposed behind the casing determined during the determining step is a bonding to the casing.

6. A method as claimed in claim 1 wherein the properties of the material disposed behind the casing are determined in the presence of a microannulus.

7. A method of determining the presence of a microannulus behind a casing in a wellbore, comprising:
using a transmitter means adapted to be disposed in said wellbore within said casing, transmitting acoustic signals into said wellbore;
using a receiver means adapted to be disposed in said wellbore within said casing, receiving at least two of said acoustic signals in said wellbore, each of said signals corresponding to different spacings between a transmitter of said transmitter means and a receiver of said receiver means;
combining said acoustic signals and deriving from each of the acoustic signals a compensated attenuation rate signal representative of an attenuation of the received acoustic signal produced while propagating axially along said casing and a coupling signal representative of an attenuation of the received acoustic signal produced while propagating between the transmitter and said casing and between the receiver and said casing; and
determining the presence of a microannulus behind the casing from a comparison of both the attenuation rate signal and the coupling signal associated with each of said received acoustic signals.

8. A method as in claim 7 wherein the said acoustic signals transmitted into said wellbore have multiple frequencies.

9. A method as in claim 8 wherein various ones of the multiple frequencies are used to further determine a size of the microannulus.

10. Apparatus for determining the properties of a material disposed behind a casing in a wellbore, comprising:
transmitter means for transmitting at least two acoustic signals into the wellbore;
receiver means for receiving the two acoustic signals in the wellbore, each said at least two acoustic signals corresponding to different spacings between a transmitter of said transmitter means and a receiver of said receiver means;
processing means for combining said at least two acoustic signals thereby producing for each acoustic signal a compensated attenuation signal representative of an attenuation of an amplitude of the received acoustic signal produced while propagating axially along said casing and a coupling signal representative of an attenuation of the amplitude of the received acoustic signal produced while propagating between said transmitter and said casing and between said receiver and said casing;
means for measuring an amplitude of each said compensated attenuation signal and coupling signal; and
means for determining the properties of the materials behind the casing from the measurements of the amplitude of both said compensated attenuation signal and said coupling signal.

11. Apparatus as claimed in claim 10 wherein the different spacings between the said transmitter means and the said receiver means include 2.5 feet and 3.5 feet.

12. Apparatus as claimed in claim 10 wherein the transmitter means has a single fundamental frequency.

13. Apparatus as claimed in claim 12 wherein the fundamental frequency is 20kHz.

14. Apparatus as claimed in claim 10 wherein the receiver means includes an array of receivers.

15. Apparatus as claimed in claim 10 wherein the transmitter means provides acoustic signals at multiple frequencies.

16. Apparatus as claimed in claim 10 wherein the transmitter means includes one acoustic transmitter and the receiver means includes at least two receivers separated from the transmitter by at least two different preselected distances.

17. Apparatus as claimed in claim 10 wherein the receiver means includes one receiver and the transmitter means includes at least two acoustic transmitters separated from the receiver by at least two different preselected distances.

* * * * *